United States Patent [19]

Gross et al.

[11] Patent Number: 5,279,544

[45] Date of Patent: Jan. 18, 1994

[54] TRANSDERMAL OR INTERDERMAL DRUG DELIVERY DEVICES

[75] Inventors: Joseph Gross, Moshav Mazor; Shlomo Zucker, Mihmoret, both of Israel

[73] Assignee: Sil Medics Ltd., Tikua, Israel

[21] Appl. No.: 981,652

[22] Filed: Nov. 25, 1992

Related U.S. Application Data

[63] Continuation-in-part of Ser. No. 850,595, Mar. 13, 1992, which is a continuation-in-part of Ser. No. 627,104, Dec. 13, 1990, Pat. No. 5,156,591.

[51] Int. Cl.⁵ .............................................. A61N 1/30
[52] U.S. Cl. ...................... 604/20; 604/145; 607/149; 607/154
[58] Field of Search .................. 604/20, 145, 290; 128/798, 802, 803

[56] References Cited

U.S. PATENT DOCUMENTS

| | | | |
|---|---|---|---|
| 4,886,514 | 12/1989 | Maget | 604/20 X |
| 4,921,475 | 5/1990 | Sibalis | 604/20 |
| 5,090,963 | 2/1992 | Gross et al. | 604/132 |

FOREIGN PATENT DOCUMENTS

| | | | |
|---|---|---|---|
| 0429842 | 6/1991 | European Pat. Off. | |
| 2562800 | 10/1985 | France | |
| 1296174 | 3/1987 | U.S.S.R. | 604/20 |

Primary Examiner—Lee S. Cohen
Assistant Examiner—Jeffrey R. Jastrzab
Attorney, Agent, or Firm—Benjamin J. Barish

[57] ABSTRACT

A transdermal drug delivery device includes a liquid reservoir for a liquid drug to be delivered, and a drug delivery body which includes a plurality of tubular elements extending through the body, each having an inlet end communicating with the liquid reservoir, and an outlet end engageable with the subject's skin to conduct the liquid drug directly to the subject's skin.

21 Claims, 3 Drawing Sheets

TRANSDERMAL OR INTERDERMAL DRUG DELIVERY DEVICES

RELATED APPLICATION

The present application is a continuation-in-part of our Patent application Ser. No. 07/850,595 filed Mar. 13, 1992, which is a continuation-in-part of 07/627,104 filed Dec. 13, 1990, now U.S. Pat. No. 5,156,591.

BACKGROUND OF THE INVENTION

The present invention relates to transdermal or interdermal drug delivery devices for delivering a liquid drug to a subject via the subject's skin. The invention is particularly useful with respect to the drug delivery device described in our U.S. Pat. No. 5,156,591, and is therefore described below with respect to that device, but it will be appreciated that the invention could advantageously be used in other types of drug delivery devices.

Our U.S. Pat. No. 5,156,591 describes a transdermal drug delivery device which delivers a drug to the subject by means of an electrically-induced mass transfer phenomenon called iontophoresis. This process for drug delivery has recently become of great interest, and many such transdermal delivery devices have been described in the patent literature, including U.S. Pat. Nos. 4,164,226, 4,640,689, 4,708,716, 4,752,285, 4,693,711, 5,057,072, U.S. Statutory Invention Registration H516, and European Patent Application Publication 0299631. Other methods of electrically-aided or electrically-controlled transdermal drug delivery devices are described in U.S. Pat. No. 4,886,513, as well as in our prior U.S. Pat. Nos. 5,062,834 and 5,090,963.

OBJECTS AND BRIEF SUMMARY OF THE INVENTION

An object of the present invention is to provide a transdermal drug delivery device which may be used in any of the foregoing types of devices and which provides an improved delivery of the drug. Another object of the invention is to provide an improved transdermal drug delivery device particularly useful in delivering the drug by an electrically-induced mass transfer phenomenon, such as iontophoresis or electrophoresis.

According to the present invention, there is provided a drug delivery device for delivering a liquid drug to a subject via the subject's skin, comprising: a housing; a liquid reservoir in the housing for a liquid drug to be delivered; and a drug delivery body of resilient deformable material carried by the housing and having one side communicating with one side of the liquid reservoir, and the opposite side exposed to engage the skin of the subject to receive the drug; characterized in that the drug delivery body includes a plurality of stiff tubular elements extending through the body, each having an inlet end communicating with the liquid reservoir, and an outlet end at said opposite side of the drug delivery body to conduct the liquid drug directly to said opposite side.

According to further features in some described embodiments, the device further includes control means for controlling the pressure in the reservoir for controlling the rate of delivery of the drug therefrom said via said plurality of stiff tubular elements extending through the drug delivery body.

In one described embodiment, the control means includes a first displaceable membrane for controlling the pressure in the reservoir in order to control the rate of delivery of the drug from the reservoir via the tubular elements to the subject's skin. Also, the drug delivery body is in the form of a second displaceable membrane through which the plurality of tubular elements extend and displaceable body pressure in the reservoir. The control means may further include an electrolytic cell capable of generating a gas to displace the first-mentioned membrane corresponding to the electrical current applied to the electrolytic cell.

According to another described embodiment, the control means includes a partition between the liquid reservoir and the drug delivery body and formed with a metering orifice for metering the flow of drug from the reservoir to the drug delivery body.

The plurality of stiff tubular elements may be in the form of hollow needles having inner diameters of less than 1 mm and projecting at least 0.1 mm from the face of the drug delivery body. Preferably, the drug delivery body includes at least fifty of such stiff tubular elements or hollow needles. Their tips may be cut at a bias to pierce the outer layer of dead cells on the skin and thereby to enhance the penetration of the drug.

In the use of the device, the plurality of tubular elements are pressed firmly against the subject's skin, and thereby provide a better delivery of the drug to the subject's skin, as compared to the use of microporous or matrix-type drug delivery bodies as in the prior art. The device also permits better control of the drug delivery rate. When the delivery is effected by iontophoresis, the better delivery of the drug enables lower electrical currents to be used, thereby decreasing the danger of burning or irritating the subject's skin.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
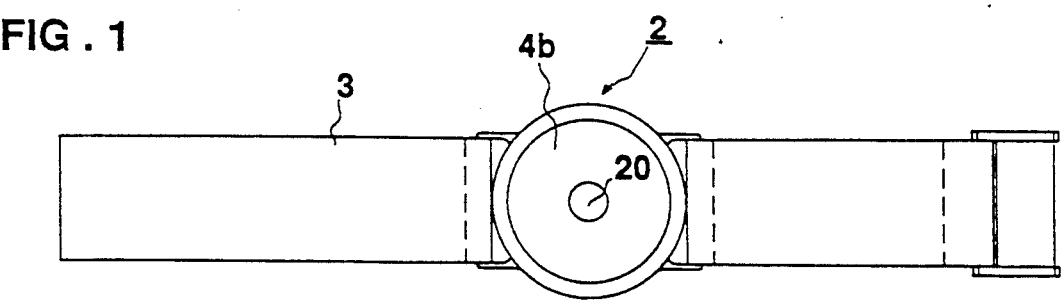
FIG. 1 is a top plan view illustrating one form of transdermal drug delivery device constructed in accordance with the present invention.
Figure 2:
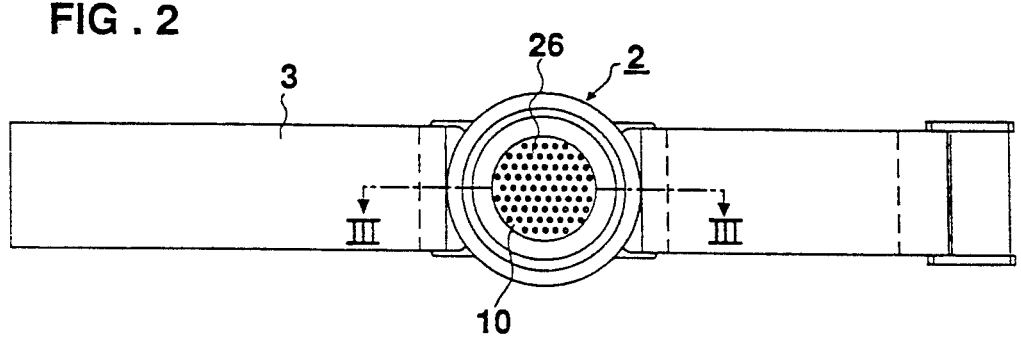
FIG. 2 is a bottom plan view of the device of FIG. 1.
Figure 3:
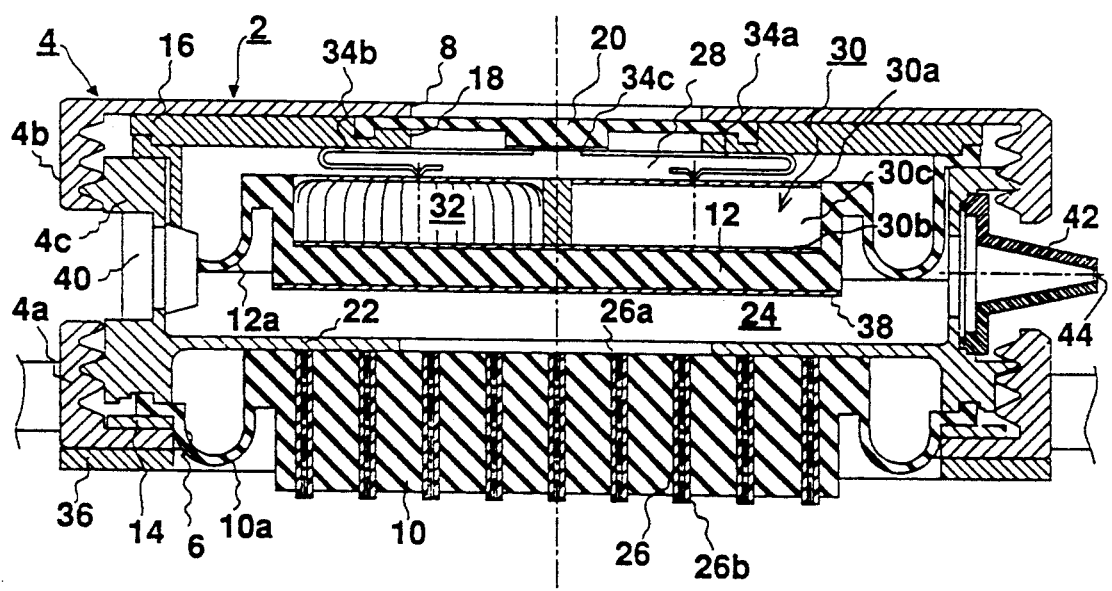
FIG. 3 is an enlarged sectional view along line III—III of FIG. 2.

The transdermal drug delivery device illustrated in FIGS. 1–3 of the drawings, and generally designated 2, is applied by a band 3 to the arm or leg of the subject, with one side of the device (that side illustrated in FIG. 2) firmly pressed against the subject's skin. The device 2 is a self-contained unit which includes a reservoir for the liquid drug to be delivered, as well as electrodes for delivering the drug by means of the iontophoresis electrically-induced mass transfer phenomenon. Device 2 further includes an electrolytic cell which, together with the iontophoresis electrodes, controls the rate of feed of the drug to the subject, and an electrical battery for powering both the iontophoresis electrodes and the electrolytic cell.

The internal structure of the transdermal drug delivery device 2 is more particularly illustrated in FIG. 3. It includes a housing 4 of plastic material and of circular configuration. Housing 4 is made of an inner section 4a, an outer section 4b, and an intermediate section 4c threadedly joining sections 4a and 4b together. The inner section 4a is formed with a large circular opening 6, and the outer section 4b is formed with a smaller circular opening 8.

An inner membrane 10 is clamped between housing sections 4a and 4c, and an outer membrane 12 is clamped between housing sections 4b and 4c. Both membranes 10 and 12 are of elastomeric material and include annular flexible sections 10a, 12a, so as to make them displaceable in response to pressure. Membrane 10 is aligned with the center opening 6 in housing section 4a and is clamped between that housing section and the intermediate section 4c via a ring 14. Membrane 12 is clamped between the intermediate housing section 4c and the outer housing section 4b via a disc 16 having a central opening 18 in alignment with opening 8 in the outer housing section 4b. A third membrane 20 is clamped between disc 16 and the outer housing section 4b to close opening 8.

Membrane 10 is displaceable outwardly of housing 4 by its annular flexible section 10a, but is restrained against inward displacement by a rigid annular disc 22 integrally formed with the intermediate housing section 4c. Membrane 12, however, is displaceable in both directions by its annular flexible section 12a. Membrane 20 is similarly displaceable in both directions with respect to openings 8 and 18 in housing section 4b and disc 16, respectively.

The two membranes 10, 12 define, between them, a chamber 24 serving as a liquid reservoir for the liquid drug to be delivered by the device 2. Membrane 10 serves as a drug delivery body through which the drug is delivered. For this purpose, membrane 10 includes a plurality of tubular elements 26 extending through it, with each tubular element having an inlet end 26a communicating with the liquid reservoir 24, and an outlet end 26b engageable with the subject's skin.

A second chamber 28 is defined between membrane 12 and disc 16 and its membrane 20. Chamber 28 serves as a pressure-control chamber for controlling the pressure applied to the drug chamber 24 for controlling the rate of feed of the liquid drug via tubular elements 26 through the drug delivery membrane 10. For this purpose, chamber 28 includes an electrolytic cell, generally designated 30, comprising a pair of electrodes 30a, 30b and an electrolyte 30c, which generate a gas in accordance with the current pressing through it from the two electrodes. Such electrolytic cells are well known and are capable of generating a gas (e.g., oxygen and/or hydrogen) when an electrical current is applied, according to the electrolyte used.

Electrolytic cell 30 is located in one side of a cavity formed in membrane 12. The other side of the cavity serves as a compartment for a button-type battery 32 powering the electrolytic cell 30. Electrode 30a of the electrolytic cell is connected to one side of the battery via spring clips 34a and 34b electrically connected together by lead 34c, all carried by disc 16; whereas electrode 30b of the electrolytic cell is extended so as to engage the other side of the battery 32.

Battery 32 also supplies electrical current to a pair of iontophoresis electrodes 36, 38, to induce the transfer of the drug within compartment 24 via the tubular elements 26 in membrane 10 to the subject's skin. Electrode 36 is of annular shape and encloses membrane 10 so as to come into contact with the subject's skin when the device 2 is applied to the subject. Electrode 38 is a conductive layer applied to membrane 12 facing the drug compartment 24 so as to come into direct contact with the drug therein.

The drug is introduced into the drug compartment 24 via an injection port 40 received in an opening on one side of the intermediate housing section 4c. A nipple 42 is threadedly applied in alignment with an opening in the opposite side of the intermediate housing section 4c and is closed by a hydrophobic filter 44. The liquid drug is introduced into drug compartment 24 via an injection syringe piercing plug 40. Nipple 42 serves as a vent for purging the air from compartment 24 until the vent is closed by contact of the liquid drug with the hydrophobic filter 44 when the compartment is filled with the drug.

Membrane 10 is made of a resilient, deformable material. The tubular elements 26 passing through membrane 10 are preferably made of a stiff, i.e., rigid or semi-rigid, plastic material having an inner diameter of less than 1.0 mm, and projecting at least 0.1 mm from the outer face of membrane 10. As examples, these tubular elements 26 may be made of Teflon (Reg. TM), or of a polycarbonate resin, have an outer diameter of 1.0 mm, an inner diameter of 0.5 mm, and projecting about 0.3 mm from the surface of the drug delivery membrane 10 in contact with the subject's skin. A drug delivery device would usually include at least 50 of such tubular elements, with the outlet ends 26b of each such element firmly engaging the subject's skin so as to effectively seal their inner channels to the subject's skin. These tubular elements thus deliver the drug from compartment 24 directly to a multitude of spaced discrete areas on the subject's skin, and at a rate determined by the pressure applied to the drug chamber 24 by the displacement of membrane 12. If desired, the tips of the tubular elements could be cut at a bias, or made conical, to pierce the layer of dead cells on the skin and thereby to enhance the penetration of the drug, as described below with respect to FIGS. 7a–7e.

As one example, membranes 10, 12 and 20 may be of a silicone rubber. Electrically-conductive layer 38 applied to membrane 12, and/or electrode 36 applied to the subject's skin, may also be of a silicone rubber, but with an electrically-conductive filler such as silver, carbon or aluminum particles.

The device illustrated in FIGS. 1–3 of the drawings may be used as follows:

The device is applied to the arm or leg of the subject to receive the drug by the use of the bands 3 such that the inner face of the device, illustrated in FIG. 2, firmly engages the subject's skin. When the device is so applied, the outer ends 26b of the stiff tubular elements 26 passing through the drug-delivery membrane 10 project slightly from the membrane and firmly engage the subject's skin.

Battery 32 supplies electrical current via an electrical switch or other control circuitry (not shown) to both the electrolytic cell electrodes 30a, 30b and to the iontophoresis electrodes 36 and 38.

The electrical current supplied to the two electrodes 30a, 30b of the electrolytic cell 30 causes the electrolyte 30c to generate a gas in accordance with the magnitude of electrical current applied to the electrolyte. This gas increases the pressure within chamber 28 to displace membrane 12 towards membrane 10, thereby increasing the pressure within the drug chamber 24. Membrane 20, having one side exposed to the pressure within chamber 28 and the other side exposed to the atmosphere, tends to regulate the pressure within chamber 28.

The displacement of membrane 12 towards the drug delivery membrane 10 forces the liquid drug from compartment 24 through the tubular elements 26 in accordance with the pressure in chamber 24. The pressure in chamber 24 also tends to displace membrane 10 outwardly, thereby more firmly pressing the outlet ends 26b of the tubular elements 26 into contact with the subject's skin. It will thus be seen that the rate of feeding of the drug from chamber 24 via tubular elements 26 to the subject's skin will be controlled by the rate of generation of gas by the electrolytic cell 30.

The transfer of the drug from compartment 24 to the subject's skin is electrically-induced by the voltage applied between the two iontophoresis electrodes 36 and 38. Thus, electrode 36 directly contacts the subject's skin, and electrode 38 directly contacts the drug within compartment 24 delivered to the subject's skin via the tubular elements 26.

It will thus be seen that the delivery of the drug from compartment 24 to the subject's skin is effected in a manner which is both efficient and controllable by controlling the electrical current supplied to the electrolytic cell 30 and also the voltage applied between the two iontophoresis electrodes 36, 38.

Figure 4:
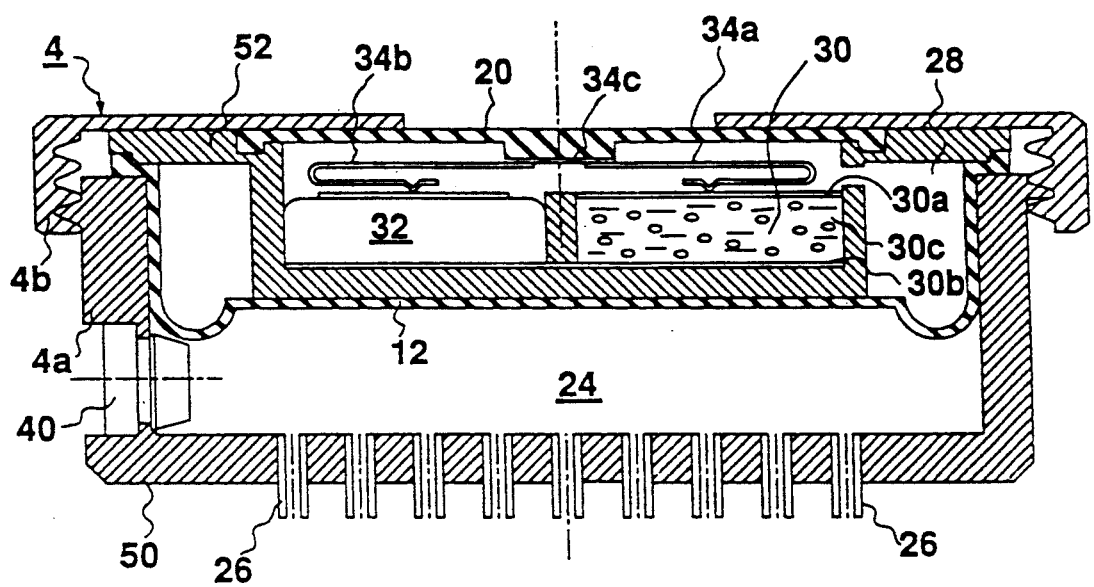
FIGS. 4, 5 and 6 are views similar to that of FIG. 3 but illustrating three further forms of drug delivery devices constructed in accordance with the present invention.

FIG. 4 illustrates another device which is generally similar to that of FIG. 3 but includes a number of changes. To facilitate understanding, the elements in the device of FIG. 4 which are generally similar to those in FIG. 3 are correspondingly numbered.

One important difference in the device of FIG. 4 over that of FIG. 3 is that the housing 4 is a two-section housing (rather than a three-section housing), including the two sections 4a and 4b threadedly secured together. The injection port 40 for introducing the drug into the drug reservoir in compartment 24 is located within an opening in housing section 4a.

Another difference in the construction of the device of FIG. 4 over that of FIG. 3 is that the drug delivery body for delivering the drug from the drug compartment 24 is constituted, not by a displaceable membrane 10, but rather by the rigid wall 50 of housing section 4a, which rigid wall carries the stiff tubular elements 26 communicating with the drug compartment 24. Thus, the device of FIG. 4 does not include a membrane corresponding to membrane 10 in FIG. 3.

The device of FIG. 4, however, does include membranes 12 and 20 defining between them the compartment for the electrolytic cell 30 and battery 32. The latter elements, instead of being received within a socket formed in membrane 12, are rather received within a socket formed in a rigid holder 52 secured between the two housing sections 4a and 4b. The electrolytic cell 30 communicates with chamber 28 between the two membranes 12 and 20, such that the pressure produced in chamber 28 by the gas generated from the electrolytic cell 30, deforms membrane 12 to control the rate of delivery of the drug via the stiff tubular elements 26.

Membrane 20, in the construction of FIG. 4, is secured between housing section 4b and the rigid holder 50 and carries electrical contact 34c on its inner face engageable with electrical contacts 34a and 34b connecting battery 32 to the electrolytic cell 30 to regulate the pressure of the gas within chamber 28. Thus, if an excessive pressure is developed within chamber 28, this will displace the center of membrane 20 outwardly, to cause its contact 34c to disengage from contacts 34a and 34b, thereby de-energizing the electrolytic cell 30 until the excessive pressure within chamber 28 drops to the point where contact 34c again engages contacts 34b and 34a to restart the generation of the gas from the electrolytic cell.

A still further difference in the construction of FIG. 4 over that of FIG. 3 is that in FIG. 4 the iontophoresis electrodes 36 and 38 are omitted. Thus, in the construction of FIG. 4, the delivery of the drug from compartment 24 via the stiff tubular elements 26 is controlled by the rate of generation of gas by electrolytic cell 30.

In substantially all other respects, the device of FIG. 4 is constructed, and operates, in substantially the same manner as described above with respect to FIG. 3.

Figure 5:
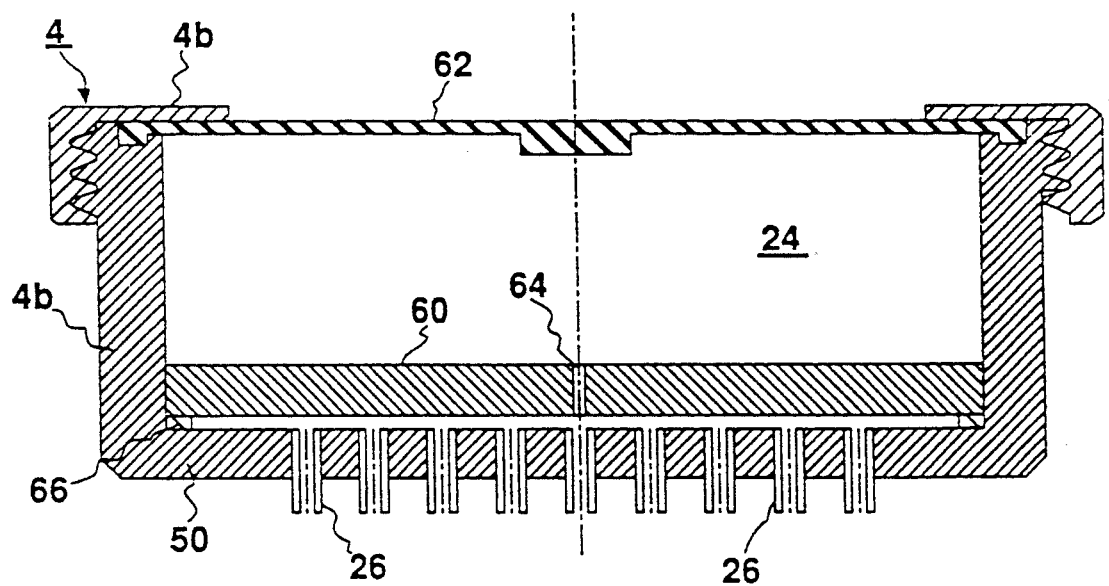

FIG. 5 illustrates another device similar to that of FIGS. 3 and 4 but further simplified in construction. To facilitate understanding, those parts which are generally similar to those included in FIGS. 3 and 4 are correspondingly numbered.

Thus, the device in FIG. 5 also includes a two-section housing 4a, 4b, as in FIG. 4, with the stiff tubular elements 28 carried by the rigid end wall 50 of housing section 4a. In FIG. 5, however, the drug reservoir compartment 24 is defined by a displaceable membrane 62, generally similar to membrane 20 in FIGS. 3 and 4, secured between the two housing sections 4a, 4b, and a partition wall 60 within the housing and formed with a metering orifice 64 for metering the flow of the drug from compartment 24 to the stiff tubular elements 28. Partition 60 is formed with an annular rib 66, or other rib formation, in order to space it from the ends of the stiff tubular elements 28 and to permit the drug to flow thereto from the reservoir in compartment 24 via the metering orifice 64.

Thus, in the construction illustrated in FIG. 5, the control of the rate of delivery of the drug via the stiff tubular elements 28 is effected by the metering orifice 64 of partition 60. Therefore, whenever it is desired to change the drug delivery rate, a partition 60 with the appropriate-size metering orifice 64 would be inserted into the housing 4.

Figure 6:
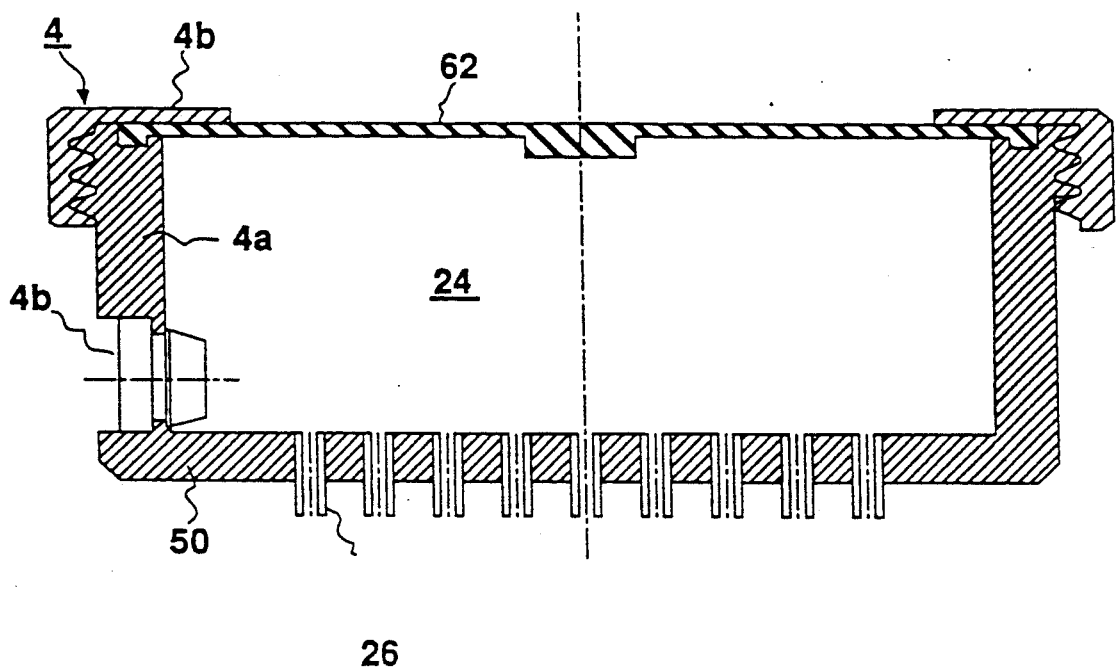

FIG. 6 illustrates another construction, similar to that of FIG. 5, but even further simplified. Those elements in FIG. 6 which are generally common to those in FIG. 5 are correspondingly numbered to facilitate understanding.

In the construction illustrated in FIG. 6, the partition 60, including its metering orifice 64, is omitted, and instead the rate of delivery of the drug is controlled by the pressure within the drug reservoir chamber 24. The drug is introduced into chamber 24, at the appropriate pressure, via injection port 40, and membrane 62 is displaced outwardly so as to apply a continuous pressure tending to urge the drug to flow from chamber 24 through the stiff tubular elements 28. If the pressure within chamber 24 drops below that needed for delivering the drug at the desired rate, an additional quantity of the drug may be introduced into compartment 24 via injection port 40.

As indicated earlier, the outer tips of the stiff tubular elements, therein designated 126, may be cut at a bias, or made conical, to pierce the layer of dead cells on the skin and thereby to enhance the penetration of the drug.

Figure 7A:
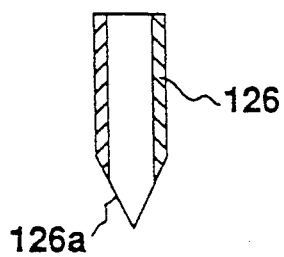
FIGS. 7a–7e illustrate various tip constructions of the stiff tubular elements extending through the drug delivery body.
Figure 7B:
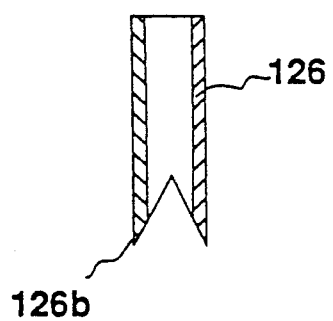
Figure 7C:
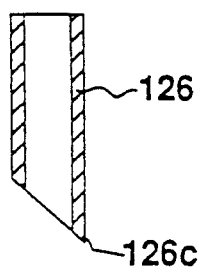
Figure 7D:
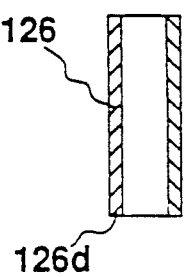
Figure 7E:
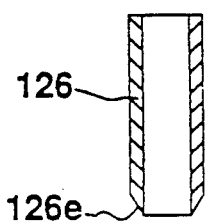

FIGS. 7a–7e illustrate various configurations of tip constructions. Thus, FIG. 7a illustrates a tip construction 126a of conical configuration; FIG. 7b illustrates the tip 126b having an inwardly-tapered cut; FIG. 7c illustrates the tip 126c as cut at a bias; FIG. 7d illustrates the tip of a flat configuration (similar to that illustrated in FIGS. 3–6); and FIG. 7e illustrates the tip 126e as being of frusto-conical configuration.

While the invention has been described with respect to several preferred embodiments, it will be appreciated that these are set forth merely for purposes of example, and that many other variations, modifications and applications of the invention may be made.

What is claimed is:

1. A drug delivery device for delivering a liquid drug to a subject via the subject's skin, comprising:
   a housing;
   a liquid reservoir in said housing for a liquid drug to be delivered;
   and a drug delivery body of resilient deformable material carried by said housing and having one side communicating with one side of the liquid reservoir, and the opposite side exposed to engage the skin of the subject to receive the drug;
   characterized in that said drug delivery body includes a plurality of stiff tubular elements extending through the body, each having an inlet end communicating with said liquid reservoir, and an outlet end at said opposite side of the drug delivery body to conduct the liquid drug directly to said opposite side.

2. The device according to claim 1, further including control means for controlling the pressure in said reservoir for controlling the rate of delivery of the drug therefrom via said plurality of stiff tubular elements extending through the drug delivery body.

3. The device according to claim 2, wherein said control means includes a first displaceable membrane for controlling the pressure in said reservoir in order to control the rate of delivery of the drug from the reservoir via said tubular elements to the subject's skin.

4. The device according to claim 3, wherein said drug delivery body is in the form of a second displaceable membrane through which said plurality of stiff tubular elements extend and which is displaceable by the pressure in said reservoir.

5. The device according to claim 4, wherein said control means further includes an electrolytic cell having electrodes and capable of generating a gas to displace said first membrane corresponding to electrical current applied to the electrodes of said electrolytic cell.

6. The device according to claim 5, wherein said housing further includes a compartment for a battery for supplying current to said electrolytic cell.

7. The device according to claim 6, wherein said housing further includes a removable cover carrying electrical contacts engageable with a battery when in said battery compartment and with one of said electrodes in the electrolytic cell when the cover is attached to the housing.

8. The device according to claim 7, wherein said cover is formed with an opening occupied by a third membrane such that one face of the third membrane is exposed to the gas generated by the electrolytic cell and the opposite face is exposed to the atmosphere.

9. The device according to claim 2, wherein said control means includes a partition between the liquid reservoir and the drug delivery body and formed with a metering orifice for metering the flow of the drug from the reservoir to said drug delivery body.

10. The device according to claim 1, wherein said plurality of stiff tubular elements have inner diameters of less than 1 mm.

11. The device according to claim 1, wherein said plurality of stiff tubular elements project at least 0.1 mm from said opposite side of the drug delivery body.

12. The device according to claim 1, wherein tips of said stiff tubular elements are cut at a bias to pierce the outer layer of dead cells on the skin and thereby to enhance the penetration of the drug.

13. The device according to claim 1, wherein said drug delivery body includes at least 50 of said stiff tubular elements.

14. A drug delivery device for delivering a liquid drug to a subject via the subject's skin, comprising:
   a housing;
   a liquid reservoir in said housing for a liquid drug to be delivered;
   a drug delivery body carried by said housing and having one side communicating with one side of the liquid reservoir, and an opposite side exposed to engage the skin of the subject to receive the drug;
   a plurality of stiff tubular elements extending through the body, each having an inlet end communicating with said liquid reservoir, and an outlet and at said opposite side of the drug delivery body to conduct the liquid drug directly to said opposite side;
   a first electrode exposed for contact with the skin of a subject;
   a second electrode in contact with the liquid drug in said reservoir;
   and means for applying a voltage between said first and second electrodes.

15. The device according to claim 10, wherein said first electrode extends around the outer periphery of the drug delivery body carrying said plurality of tubular elements.

16. A transdermal drug delivery device for delivering a liquid drug to a subject via the subject's skin, comprising:
   a housing attachable to the subject's body;
   a liquid reservoir in said housing for a liquid drug to be delivered;
   a drug delivery body carried by said housing and having one side communicating with one side of the liquid reservoir and the opposite side exposed to engage the skin of the subject to receive the drug;
   a plurality of stiff tubular elements extending through said body, each having an inlet end communicating with said liquid reservoir and an outlet end engageable with the subject's skin;
   and control means including a displaceable membrane for controlling the rate of delivery of the drug from said reservoir via said tubular elements to the subject's skin at a rate controlled by the displacement of said membrane.

17. The device according to claim 16 wherein said drug delivery body includes at least 50 of aid stiff tubular elements each having inner diameters of less than 1 mm.

18. The device according to claim 17, wherein said drug delivery body is of resilient, deformable material.

19. The device according to claim 16, wherein said housing further includes a first electrode exposed for contact with the skin of a subject, a second electrode in contact with the liquid drug in said reservoir, and means for applying a voltage between said first and second electrodes.

20. The device according to claim 19, wherein said first electrode extends around the outer periphery of the drug delivery body carrying said plurality of tubular elements.

21. The device according to claim 19, wherein said first and second electrodes are of a silicone polymer containing an electrically-conductive filler.

* * * * *